(12) United States Patent
Isken et al.

(10) Patent No.: US 11,988,643 B2
(45) Date of Patent: May 21, 2024

(54) CHARACTERIZATION OF A PHASE SEPARATION OF A COATING COMPOSITION

(71) Applicant: EVONIK OPERATIONS GMBH, Essen (DE)

(72) Inventors: Philipp Isken, Altenberge (DE); Claudia Bramlage, Essen (DE); Sandra Bittorf, Witten (DE); Oliver Kroehl, Cologne (DE); Stefan Silber, Krefeld (DE); Gaetano Blanda, Haltern am See (DE); Olivia Lewis, Berlin (DE)

(73) Assignee: Evonik Operations GmbH, Essen (DE)

( * ) Notice: Subject to any disclaimer, the term of this patent is extended or adjusted under 35 U.S.C. 154(b) by 469 days.

(21) Appl. No.: 17/476,785

(22) Filed: Sep. 16, 2021

(65) Prior Publication Data

US 2022/0082484 A1    Mar. 17, 2022

(30) Foreign Application Priority Data

Sep. 17, 2020 (EP) .................................... 20196658

(51) Int. Cl.
    *G01F 1/00*          (2022.01)
    *G01F 23/00*        (2022.01)
    (Continued)

(52) U.S. Cl.
    CPC .............. *G01N 3/08* (2013.01); *G01F 1/007* (2013.01); *G01F 23/0046* (2013.01);
    (Continued)

(58) Field of Classification Search
    CPC .. G01F 23/22; G01N 2203/0676; G01N 3/08; G01N 3/02; G01N 33/32;
    (Continued)

(56) References Cited

U.S. PATENT DOCUMENTS 6,462,813 B1    10/2002    Haven et al.
2017/0069075 A1    3/2017    Okuda
(Continued)

FOREIGN PATENT DOCUMENTS

| JP | S55-57115 A | 4/1980 | |
| KR | 2017-0030878 A | 3/2017 | |
| WO | WO-2009030268 A1 * | 3/2009 | ............... G01N 1/34 |

OTHER PUBLICATIONS

Partial European Search Report dated Jun. 8, 2021 for corresponding European Application No. 20196658.7.
(Continued)

*Primary Examiner* — Jonathan M Dunlap
(74) *Attorney, Agent, or Firm* — Harness, Dickey & Pierce, P.L.C.

(57) ABSTRACT

A method for detecting a phase separation of a waterborne or solvent-borne or solvent-free coating composition includes providing the coating composition in a receptacle; providing a measurement instrument for receiving the receptacle, the measurement instrument including a measurement probe; controlling the measurement instrument to a) displace the measurement probe through the coating composition along a predefined measurement path with a predefined speed profile, the predefined measurement path extending along a length axis of the receptacle, b) acquire a force-displacement profile by measuring a force exercised on the measurement probe while the probe is being displaced along the predefined measurement path with the predefined speed profile; processing the force-displacement profile for detecting at least one phase separation of the coating composition; and outputting a detection result.

15 Claims, 5 Drawing Sheets

(51) Int. Cl.
  *G01F 23/22* (2006.01)
  *G01N 3/02* (2006.01)
  *G01N 3/08* (2006.01)
  *G01N 15/00* (2024.01)
  *G01N 33/32* (2006.01)
(52) U.S. Cl.
  CPC ............... *G01F 23/22* (2013.01); *G01N 3/02* (2013.01); *G01N 2015/0023* (2013.01); *G01N 2015/003* (2013.01); *G01N 2015/0034* (2013.01); *G01N 2015/0042* (2013.01); *G01N 2015/0053* (2013.01); *G01N 2015/0057* (2013.01); *G01N 33/32* (2013.01); *G01N 2203/0098* (2013.01); *G01N 2203/0676* (2013.01)
(58) Field of Classification Search
  CPC ..... G01N 2015/003; G01N 2015/0053; G01N 2015/0057; G01N 2015/0023; G01N 2015/0042; G01N 2015/0034
  See application file for complete search history.

(56) References Cited

U.S. PATENT DOCUMENTS

| | | |
|---|---|---|
| 2020/0166909 A1 | 5/2020 | Noone et al. |
| 2020/0210635 A1 | 7/2020 | Washburn et al. |
| 2020/0257933 A1 | 8/2020 | Steingrimsson et al. |
| 2024/0003729 A1* | 1/2024 | Maugé ................... G01F 23/00 |

OTHER PUBLICATIONS

M. Salvador et al. 'Automatic Composition and Optimization of Multicomponent Predictive Systems With an Extended Auto-WEKA' *IEEE Transactions on Automation Science and Engineering*, vol. 16, No. 2, 2019, pp. 946-959.

Office action dated Jan. 17, 2024, issued in corresponding U.S. Appl. No. 17/476,983.

* cited by examiner

CHARACTERIZATION OF A PHASE SEPARATION OF A COATING COMPOSITION

CROSS-REFERENCE TO RELATED APPLICATIONS

This is application is based on and claims priority under 35 U.S.C. § 119 to EP Application No. 20196658.7, filed Sep. 17, 2020, the entire contents of each of which are hereby incorporated by reference.

TECHNICAL FIELD

The invention relates to the detection of phase separation of a waterborne or solvent-borne or solvent-free coating composition and to the characterization of coating compositions, in particular waterborne or solvent-borne or solvent-free coating compositions.

BACKGROUND

From manufacture through storage and processing to drying or curing after application, many different demands are made on coating compositions, related e.g. to their flow behavior. It influences the leveling, the settling/sedimentation (important for storage stability) and the film forming of the coating composition.

Coating compositions comprise components which tend to settle after a certain time, thereby forming different phases. This may result in a separation into a nearly solid phase (sediment phase) and a liquid phase, several liquid phases, or a combination of these. Phase separation may negatively influence the further processing of the coating composition since the re-dispersion of components may be difficult or incomplete, requires methods and thus time and money. Further, as multiple phases can occur simultaneously, they can influence each other. To assess the quality in terms of storage stability, the proportions of the different phases of the composition are thus determined. To investigate and avoid these problems, formulations are stored during formulation development and examined for phases. Both settling and syneresis are the result of the insufficiency of stabilization of two or more components, for example between a pigment and its solvent. What happens is that one or several components are driven away from (or out of) others and thus turn into a settlement or a syneresis, depending on the specific gravity of the component.

Since after syneresis the top liquid phase is visually recognizable as it typically contains no pigments or low pigment concentration, it may be quantitatively assessed. The phase transition for the pigmented phase and the sediment phase is however usually not optically recognizable, therefore the amount of the pigmented phase and the sediment phase cannot be easily determined quantitatively. As the sediment phase cannot usually be distinguished optically from the pigmented phase, this method may not be used to determine the amounts of the pigmented phase and the sediment phase. Therefore, attempts are made to detect the sediment phase using a spatula. To determine whether a sediment phase has formed, the spatula is scraped over the bottom of the sample glass (receptacle). This, however, allows only a very rough characterization as e.g. no sediment phase, a small or large sediment phase and/or a soft or hard sediment phase.

Due to the number of interdependent process parameters, large number of coating compositions, pretreatment approaches and surface types to which the composition is to be applied, it is currently impossible to predict whether or not a particular coating composition will provide a coating of acceptable storage stability quality. Therefore, the storage stability quality can currently only be determined retrospectively.

Currently, the storage stability is assessed visually by a human being, e.g. an employee. This purely visual assessment is typically very coarse-grained, highly subjective, and hardly reproducible. As a consequence, the identification of phases and the assessment of the quality of the surface coating may require a great deal of experience on the part of the employee but may nevertheless vary strongly from person to person which makes it difficult to compare the results. In addition, the manual evaluation of coating compositions is time-consuming and hence expensive.

SUMMARY

The invention aims at providing improved methods and a corresponding system for the characterization of a phase separation of coating composition, in particular a waterborne or solvent-borne or solvent-free coating composition, and to the use of the resulting programs and information in the context of the manufacturing of coating compositions as specified in the independent claims. Embodiments are given in the dependent claims. Embodiments of the present invention may be freely combined with each other, provided they are not mutually exclusive.

In one aspect, the invention relates to a method for detecting a phase separation of a waterborne or solvent-borne or solvent-free coating composition. The method comprises:

providing the coating composition in a receptacle;
    providing a measurement instrument for receiving the receptacle, the measurement instrument comprising a measurement probe;
    controlling the measurement instrument to
        a) displace the measurement probe through the coating composition along a predefined measurement path with a predefined speed profile, the predefined measurement path extending along a length axis of the receptacle,
        b) acquiring a force-displacement profile by measuring a force exercised on the measurement probe while the probe is being displaced along the predefined measurement path with the predefined speed profile;
    processing the force-displacement profile for detecting at least one phase separation of the coating composition; and
    outputting a detection result.

Embodiments of the invention may have the advantage that a phase separation of a coating composition may be detected by means of an acquired force-displacement profile.

The provided coating composition may be a waterborne or solvent-borne or solvent-free coating composition, which has been stored within a receptacle for a defined length of time and at a defined temperature. The storage condition of the coating composition may be that the coating composition is stored for two weeks at 50° C.

The force-displacement profile can be acquired in a reproducible, objective and fast manner, as a measurement probe of a measurement instrument for receiving a receptacle with the coating composition is displaced through the coating composition along a predefined measurement path with a predefined speed profile.

The receptacle is a container in which the coating composition is stored. The receptacle may have a removable lid, which may be removed (shortly) before the acquisition of the force-displacement profile.

By displacing the measurement probe through the coating composition along a predefined measurement path, a force, in particular a force which is proportional to the dynamic pressure, is measured. The predefined measurement path is the path covered by the measuring probe through the coating composition. The path is advantageously a straight path, wherein the measurement probe is guided from above into and through the coating composition. The measured force results from the dynamic pressure exercised by the coating composition onto the measurement probe.

The predefined speed profile of the displacement of the measurement probe may comprise a constant speed, a positive and/or negative acceleration, or one or more sections of the speed profile may comprise a constant speed and one or more sections of the speed profile may comprise an acceleration. The on the measurement probe exercised force, while the probe is being displaced along the predefined measurement path with the predefined speed profile, is recorded.

The force-displacement profile is acquired by measuring multiple forces exercised on the measurement probe while the probe is being displaced along the predefined measurement path with the predefined speed profile. The multiple measured forces may be visualized as a curve.

The processing of the force-displacement profile for detecting at least one phase separation of the coating composition may be performed manually or automatically, by detecting changes in the recorded force-displacement profile.

For example, immersion of the probe from the gas phase, e.g. ambient air, in the coating composition would lead to a sudden increase in dynamic pressure and thus a sudden increase in the recorded force-displacement profile. Therefore, a phase transition may be detected between a gas phase and a liquid phase by the sudden increase in dynamic pressure. In case that no further increase in the force-displacement profile of the coating composition can be detected, the output result may indicate that the coating composition is free of a further phase separation, other than the phase separation between the gas phase and the liquid phase. Likewise, different liquid phases with different densities and thus different dynamic pressures may be detected by an increase in the force-displacement profile. Furthermore, since the receptacle, the amount of coating composition, the predefined measurement path and the predefined speed profile may be known, the increases may be used to calculate which phase has which volume.

Embodiments of the invention may be advantageous in particular in the context of production of waterborne or solvent-borne or solvent-free coating composition, as e.g. paints, varnishes, printing inks, grinding resins, pigment concentrates and other coating materials, since a reproducible, objective characterization of phases within respective coating compositions was previously not available.

A prediction of the coating composition quality, which comprises the storage stability of the coating composition, was not possible due to the large number of components and their interactions. For example, dispersants (also known as dispersing additives or dispersing agents) are generally used for the dispersion of solids (e.g. pigments, fillers or dyes) in liquid media in order to achieve effective dispersion of the solids, reduce the mechanical shear forces required for dispersion and at the same time achieve the highest possible filling levels. The dispersing agents support the breaking up of agglomerates, wet and/or coat as surface-active materials the surface of the solids or particles to be dispersed and stabilize them against undesired re-agglomeration. In the manufacture of paints, coatings, printing inks, grinding resins, pigment concentrates and other coating materials, dispersing agents facilitate the incorporation of solids, such as pigments, dyes and fillers, which, as important components, significantly determine the optical appearance and the physico-chemical properties of such systems.

Further, for example, in solvent borne formulations, the flow properties can be regulated via the molecular weight of the dissolved binder. In waterborne formulations, the binder is in the form of dispersed polymer particles so that regulation of the flow behavior by changing the molecular weight is not possible. Rheological additives must therefore be used to adjust the flow properties of waterborne coating composition.

Applicational properties of coatings are associated with different shear rates. When stirring (dispersing), low viscosities are necessary, but storage should preferably take place at high viscosity so that the pigments are prevented from settling out. For spray application, the viscosity of the paint should be as low as possible but as soon as the paint is applied on the surface the viscosity should increase to prevent sagging on vertical substrates.

For optimum utilization, the solids must be distributed evenly in the compositions on the one hand, and on the other hand, the distribution once achieved must be stabilized. A large number of different substances are used today as dispersing agents, as rheological additives, as a binder, as a solvent which can have a considerable influence on the optical properties, quality, and storage stability of a coating composition.

According to embodiments, the processing of the force-displacement profile comprises evaluation of the force-displacement profile for specific features being indicative of at least one phase separation.

Embodiments of the invention may have the advantage that the processing of the force-displacement profile comprises a thresholding operation, change point detection, knee/elbow point detection, and/or the application of the Ramer-Douglas-Peucker algorithm (RDP) or isolation forest for detecting the phase separations.

For the detection of a phase separation a threshold operation may be used, whereby a threshold value may be set manually, automatically assigned to an increase in dynamic pressure or determined visually by analyzing the force-displacement profile and detecting an increase in dynamic pressure. The threshold value may be set in accordance with the used solvent and/or other further components of the coating composition.

Further, to determine a phase separation, a change point detection may be used. By using change point detection positions on the graph/diagram where the probability distribution of the stochastic process or time series changes may be identified. Also, isolation forest may be used to determine a phase separation, as isolation forest is an unsupervised learning algorithm for anomaly detection that works on the principle of isolating anomalies (here changes). Furthermore, for the determination of a phase separation, a knee/elbow point detection may be used for detecting inward or outward curved kinks in the graph, which are referred to as knees or elbows. Also, a Ramer-Douglas-Peucker algorithm (RDP) may be used to determine a phase separation, as RDP is an algorithm that provides piecewise approximations, constructs an approximated trajectory and finds "valuable"

turning points in the force-displacement profile. RDP may be used for reducing the number of points in a curve, here force-displacement profile that is approximated by a series of points.

Applicant has observed that thresholding operation, RDP and change point detection are best suited for the detection of phase separations.

For example, the phase separation of the coating composition may be detected from a force-displacement profile, which may be shown in a diagram, wherein the height of the measuring probe in a receptacle is shown on the X-axis and the measured force is shown on the Y-axis, as follows:

Calculating the average of the recorded force for the first section of the measurement. The first section comprises the measurements of the force recorded from the start of the measurement to the first force-displacement pattern or the first increase in the force-displacement profile. In the first section the measuring probe is not yet immersed in the sample and the measurement is performed in air. Therefore, only the background noise is measured.

Shifting the recorded force-displacement profile (curve) by the previously calculated average value. Therefore, the noise may be around zero on the Y-axis.

Determining the end of the first phase. The end of the first phase is defined as the first measuring point at which the force exceeds a determined first threshold value (e.g. 0.03 N).

Determining the beginning of the first phase using the recorded force-displacement profile (curve), starting from the end of the first phase going backwards to the beginning of the measurement. The beginning of the first phase is defined as the first measuring point in this direction at which the force falls below a determined second threshold value (e.g. 0.002 N)

The length of the phase is calculated from the difference of the X-values of these two threshold values (force-displacement patterns).

Optionally or in addition, the determination of a possible sediment phase may be carried out analogous to the phase-separation identification, as described in the previous steps. The beginning (boundary) of the sediment phase may be detected when a determined threshold value is exceeded. From the X-value (height) of this measuring point the amount of the sediment phase may be calculated as difference if the height of the receptacle bottom is known.

Embodiments of the invention may provide that the phase separations of the coating composition comprise at least two liquid phases, a first phase and a second phase, wherein the second phase contains more fillers and/or pigments (pigmented phase) than the first phase (herein referred as syneresis).

Optionally or in addition, the determination of a possible pigmented phase (second liquid phase) may be carried out analogous to the phase-separation identification, as described above. The beginning (boundary) of the pigmented phase may be defined as the end of the first phase (starting point of pigmented phase). The end of the pigmented phase may be defined as the beginning of the sediment phase if any or the receptacle bottom (end point of pigmented phase). The length of the pigmented phase is calculated from the difference of these two points.

The ratio of the lengths of each of the phases to the total length of the coating composition may give an information of the stability of coating composition. For example, the first phase has a length of 8 mm and the total length of the coating composition is 20 mm. The ratio of the first phase is calculated as 40 vol % which indicates a low storage stability of the coating composition.

Suitable fillers are, for example, those based on kaolin, talc, mica, other silicates, quartz, cristobalite, wollastonite, perlite, diatomaceous earth, fibrous fillers, aluminium hydroxide, barium sulfate, glass or calcium carbonate.

Preferably, the pigments are organic or inorganic pigments or carbon black pigments. Examples of inorganic pigments include iron oxides, chromium oxides or titanium oxides. Suitable organic pigments are, for example, azo pigments, metal complex pigments, anthraquinoid pigments, phthalocyanine pigments, and polycyclic pigments, especially those of the thioindigo, quinacridone, dioxazine, pyrrolopyrrole, naphthalenetetracarboxylic acid, perylene, isoamidolin(on)e, flavanthrone, pyranthrone or isoviolanthrone series. Carbon blacks used may be gas blacks, lamp blacks or furnace blacks. These carbon blacks may additionally be post-oxidized and/or converted to beads.

Since the second phase contains more fillers and/or pigments, the dynamic pressure in the second phase is higher than the dynamic pressure in the first phase, which may contain less fillers and/or pigments.

According to some embodiments, the second phase comprises a filler and/or pigments-containing liquid sub-phase and a sediment sub-phase.

The method may then comprise
aborting the acquisition of the force-displacement profile when the measured force reaches or surpasses a predefined limit, the displacement of the probe when the predefined limit is reached being indicative of the commencement of the sediment sub-phase.

In this way it is advantageously achieved that the measuring probe does not collide with the sediment phase or penetrate into the sediment phase. This may reduce or eliminate the risk of damage to the measuring probe or measurement instrument.

In a further embodiment, the method may comprise:
calculating a measure for the recognized phases for providing a qualitative and/or quantitative characterization of the coating composition, in particular the measure being
a quantitative measure selected from a group comprising: the length of the measurement path between two detected phase boundaries, the traveling time of the measurement probe between two detected phase boundaries, the relative sizes of the detected phases, the number of detected phases; and/or
a qualitative measure, the qualitative measure being in particular the type of the phase selected from a group comprising a gas phase, a first phase, and a second phase, wherein optionally the second phase contains more fillers and/or pigments than the first phase and/or optionally the second phase comprises a filler and/or pigments-containing liquid sub-phase and a sediment sub-phase; and
outputting the qualitative and/or quantitative characterization of the coating composition.

In a further aspect, the invention relates to a method for detecting a phase separation of a waterborne or solventborne or solvent-free coating composition. The method comprises:
processing a force-displacement profile by a phase-separation-identification program, the phase-separation-identification program being configured to recognize force-displacement patterns, each force-displacement pattern being assigned to a boundary of a type of phase; and providing a detection result of one or more phases recognized by the phase-separation-identification program.

Embodiments of the invention may have the advantage that a characterization of coating composition phases is provided by means of a phase-separation-identification program and hence in a reproducible, objective, and fast manner. Individual phases in a coating composition are detected fully automatically and used for automatically computing a characterization of the coating composition in dependence on the type and/or extent (quantity) of the one or more phases identified in the force-displacement profile analysis procedure. Hence, a large number of force-displacement profiles can be evaluated and annotated with the automatically computed characterization of the respectively described coating composition fully automatically. This may be particularly useful in the context of a high throughput facility for testing and/or manufacturing coating compositions. The automated determination of the coating composition characterization increases the transparency and reproducibility of the assessment of the quality and other properties of the coating composition.

Embodiments of the invention may have the further advantage that the automatically identified coating composition phases and the characterization of the coating composition derived therefrom can be used as databases for performing many different forms of data analysis. In particular, the computed characterizations can be used as a qualitative and/or quantitative indicator of the quality of the coating composition, the coating composition storage stability and/or the coating composition manufacturing process used for manufacturing the coating composition.

The automated computation of qualitative and/or quantitative coating composition characterizations may enable an automated analysis of large amounts of data and may ensure comparability of the quality characterizations of different coating compositions, and/or coating manufacturing process parameters. This is particularly useful in the context of producing and testing many different varieties of a coating composition to identify the optimum coating composition for good storage quality.

Embodiments of the invention may be advantageous in particular in the context of the production of a waterborne or solvent-borne or solvent-free coating compositions, as e.g. paints, varnishes, printing inks, grinding resins, pigment concentrates and other coating materials, since a reproducible, objective characterization of possible phase formation within respective coating compositions was previously not available. A prediction of the coating composition quality was not possible due to the large number of components and their interactions According to some embodiments, the characterizations of the coating compositions provided by the phase-separation-identification program comprises fine-granular quantitative characterizations, e.g. a numerical value within a continuous scale or within a set of at least 10 different predefined numerical values or value ranges. The phase-separation-identification program is configured to transform the fine-granular quantitative characterizations into coarse-granular quantitative characterizations to make the automatically computed characterizations comparable to an existing, coarse-grained data set. For example, the existing, coarse-grained data set may have been created manually. The coarse-granular quantitative characterization can be a numerical value within a set of less than 10 different predefined numerical or categorical values or value ranges. The automated transformation may increase the data basis for various data analysis or machine learning purposes by proving a mix of manually labeled and automatically labeled force-displacement profiles of coating compositions which are comparable to each other.

According to embodiments, the method comprises calculating, by the phase-separation-identification program, a measure for the recognized phases for providing a qualitative and/or quantitative characterization of the coating composition; and outputting the qualitative and/or quantitative characterization of the coating composition.

For example, a coating composition may comprise two or more phases of one or more different phase types and of varying extents. The calculated qualitative and/or quantitative measures of each of the phases can be used, e.g. aggregated, for obtaining a qualitative and/or quantitative characterization of the coating composition which integrates the automatically obtained measures of the automatically identified phases in the coating composition.

The identification of individual phases and the automated determination of the measures of the individual phases may have the advantage that both the number, the type, the amount, and further properties of each individual phase in a coating composition is objectivized. Embodiments of the invention are much less subjective than prior art approaches based on manual/visual assessment of individual phases and/or coating composition qualities by the staff. The visual evaluation was not quantitative and only allowed a very rough classification of the results according to coarse-grained quality classes or a coarse-grained grading system.

For phase separation where the different phases can be recognized visually, current methods allow a quantitative or semi-quantitative analysis of the amounts of the different phases by measuring the height of each phase. However, this is a manual and time-consuming process. Besides that, the phase boundary is especially for pigmented or filled phases not always clearly detectable, which decreases the accuracy of the detection and can even lead to cases where the phase separation cannot be detected visually.

According to embodiments, the measure of the phase is or comprises a quantitative measure selected from a group comprising: the length of the measurement path between two neighboring detected force-displacement patterns, the traveling time of the measurement probe between two neighboring detected force-displacement patterns, or calculated measures like the relative heights of the different phases, the number of detected force-displacement patterns.

In addition, or alternatively, the measure is or comprises a quantitative measure. The quantitative measure can in particular be the type of the phase identified. For example, the phase can be selected from a group comprising a gas phase, a first liquid phase, and a second liquid phase. The second liquid phase may contain more fillers and/or pigments than the first liquid phase. The second liquid phase may comprise a filler and/or pigments-containing liquid sub-phase and a sediment sub-phase.

According to embodiments, the method further comprises:
   providing a waterborne or solvent-borne or solvent-free coating composition in a receptacle;
   providing a measurement instrument for receiving the receptacle, the measurement instrument comprising a measurement probe;
   positioning of the measurement probe relative to, in particular above, the coating composition in the receptacle;
   controlling the measurement instrument to displace the measurement probe through the coating composition along a predefined measurement path with a predefined speed profile, the predefined measurement path extending along a length axis of the receptacle, while displacing of the measurement probe through the coating composition, using the measurement probe for acquiring a force-displacement profile by measuring a force exercised on the measurement probe while the probe is being displaced along the predefined measurement path with the predefined speed profile.

The features waterborne or solvent-borne or solvent-free coating composition, the receptacle, the measurement instrument, measurement probe, the predefined measurement path, the predefined speed profile and the force-displacement profile may be the same features as disclosed above for the method for detecting a phase separation of a waterborne or solvent-borne or solvent-free coating composition.

Embodiments of the invention which control the predefined measurement path and the predefined speed profile of the measurement probe may have the advantage that the force-displacement profiles can be provided as input to the phase-separation-identification program. In case the phase-separation-identification program was obtained based on a machine learning approach, embodiments of the invention controlling the predefined measurement path and the predefined speed profile of the measurement probe may ensure that the conditions used for acquiring the force-displacement profile are similar to the conditions used for obtaining the training force-displacement profiles from which the phase-separation-identification program was derived. By controlling the force-displacement profile acquisition process, embodiments may ensure that the acquired force-displacement profiles are comparable and can be processed by the phase-separation-identification program reproducibility and accurately.

According to embodiments, the processing of the force-displacement profile further comprises:
- performing, by the phase-separation-identification program, a method selected from a thresholding operation, change point detection, isolation forest, knee/elbow detection, and/or the Ramer-Douglas-Peucker algorithm (RDP) or such, on the force-displacement profile, thereby automatically labeling force-displacement patterns to the type of phase and the instance of this type of phase in the force-displacement profile; and
- outputting the one or more identified phase instances.

For example, the identified force-displacement patterns can be output as coordinates.

Outputting coordinates (e.g. in the form of x and y coordinates of the force-displacement patterns forming the boundary of the phases) may have the advantage that these coordinates can be further-processed easily by the phase-separation-identification program, e.g. for computing the fractional of phases of a force-displacement profile curve. On the other hand, providing a graphical representation of the pattern instances may have the advantage that the identified phases can be easily recognized by a human being. For example, the phase-separation-identification program can generate a graphical user interface (GUI) configured to display image segments having been identified to represent a phase of a particular type by a respective force-displacement pattern. Providing a combination of coordinate information and a graphical representation may have the advantage that the output of the phase-separation-identification program can easily be processed and interpreted both by software and humans.

According to embodiments, the method further comprises installing and/or instantiating the phase-separation-identification program on a data processing system comprising a graphical user interface (GUI), the data processing system is operatively coupled to the measurement probe of a measurement instrument for receiving the receptacle. The phase-separation-identification program can be configured to generate a GUI which is displayed to a user via a screen of the data processing system. In response to a user action via the GUI, the phase-separation-identification program acquires the force-displacement profile of the coating composition by the phase-separation-identification program via the measurement probe. The phase-separation-identification program uses the acquired force-displacement profile as the force-displacement profile that is processed by the phase-separation-identification program for automatically identifying the type of phase, for computing the measures of the type of phase and for computing the qualitative and/or quantitative characterization of the coating composition. Then, the phase-separation-identification program performs the outputting of the computed characterization via the GUI or another output interface of the data processing device.

According to embodiments, the phase-separation-identification program is selected from a group comprising:
- an application program, the data processing device being a portable or stationary device specially designed for detection of phase separations; for example, the specially designed quality control device can comprises additional components such as a measurement probe whose position relative to the coating composition can be controlled by the phase-separation-identification program; embodiments of the invention may ensure that these devices are able to automatically identify and characterize coating composition phases and the quality of the examined coating compositions in a reproducible and accurate manner;
- an application program, the data processing device being a high-throughput (HT) facility (also referred to as "high throughput equipment"—HTE) for the automated or semi-automated manufacturing of coatings; in particular, the high throughput facility can be a facility comprising an automated force-displacement profile acquisition unit as described herein for embodiments of the invention; using the phase-separation-identification program in the context of an HT-facility may be particularly advantageous, because HT-facilities are able to automatically manufacture and test many different coating compositions, thereby creating large amounts of data which again can be used for training a machine learning program to identify and/or predict coating compositions having desired coating quality characterizations; automatically generating and storing qualitative and/or quantitative coating characterizations in the context of an HT-facility may allow to consider coating phases and coating quality characterizations in various big data applications, in particular machine learning based predictions; this was not possible based on manually created, subjective and inconsistent quality labels;
- a web application downloaded and/or instantiated permanently or temporarily via a network; for example, a server can provide a Java application implementing the phase-separation-identification program via the Internet; or
- a program executed within a browser, e.g. a JavaScript program. In respect to the web application and the browser program, it is possible that the phase-separation-identification program is implemented as a client-server-system, wherein the client part instantiated on the data processing system is responsible for acquiring a force-displacement profile in sufficient quality and in an appropriate context and wherein the server part is instantiated on a remote server computer and is responsible for performing the force-displacement profile analysis for identifying the phases and for providing the coating composition characterization.

According to embodiments, the phase-separation-identification program comprises a predictive model having learned from training data in a training step using a machine learning program to recognize the predefined patterns. In particular, the machine learning program can be a neural network.

According to embodiments, the training data comprises multiple labeled training force-displacement profiles of multiple coating compositions. For example, the training force-displacement profiles can comprise force-displacement profiles for many different coating compositions, whereby the different coating compositions have been obtained by combining different types and/or amounts of components and/or by combining the components according to different manufacturing process parameters (e.g. mixing duration, mixing temperature, mixing speed, etc.). Hence, the training data may cover a huge, multidimensional data space covering a variety of different coating compositions and coating composition manufacturing parameters. The method further comprises storing the training data in a database. Initially, the labels of the training data will be manually annotated. In later training steps, the training data may be extended by additional force-displacement profiles of coating compositions which have been automatically labeled and which are preferably checked or corrected by a human annotator. The labels preferably comprise an indication of the boundaries of phases, the type phase, and/or one or more other characterizations of the coating composition which in some cases may be identical to measures of the one or more phases depicted in the respective training force-displacement profile.

The above-mentioned steps describe how the already existing and/or trained phase-separation-identification program can be applied on new (test) force-displacement profiles which do not comprise a label indicating the occurrence, type or extend/amount of phases. In the following, embodiments of a method for generating and training the predictive model of the phase identification software are described. The test phase and the training phase can be performed on the same or on different data processing systems. For example, it is possible to train the model M1 on a first data processing system, integrate the trained model M1 in a phase-separation-identification program which may comprise some additional functions or modules, e.g. for interacting with a user and/or with a facility for manufacturing or testing coatings, and transfer the phase-separation-identification program to a second data processing system.

Training Phase of the Model (M1) of the Phase-Separation-Identification Program

According to embodiments, the method comprises performing the training step on the training data, the training data comprising a set of labeled digital training force-displacement profiles of coating compositions, the labels identifying the location/positions and type of phases in the training force-displacement profiles. The predictive model is trained for recognizing the pattern by means of the labeled training force-displacement profiles using back propagation.

Providing the phase-separation-identification program in the machine learning process may have the advantage that the generated predictive model will have learned a plurality of highly complex interrelations between a plurality of different factors comprising type and/or amount of coating components and/or coating composition manufacturing parameters.

According to embodiments, each of the training force-displacement profiles has assigned additional data being processed in the training step for enabling the predictive model to correlate the additional data with the force-displacement patterns (and with the measures of the phases and/or the quantitative and/or qualitative characterizations of the coating composition). The additional data comprise context data, wherein the context data comprises:

one or more components of the coating composition used for generating the coating composition for which the training force-displacement profile has been acquired; the specification of the one or more components of the coating composition may comprise a specification of the type and/or amount of the component; for example, the information regarding the component provided as context data can comprise the type and/or amount of dispersion agent and/or the type or amount of a rheology modifier and/or the type or amount of one or more pigments and/or the type and amount of solvent; and/or one or more manufacturing-process parameters, the manufacturing-process parameters characterizing a process of generating a coating composition, the process parameters for example comprising mixing speed, the mixing temperature, and/or the mixing duration of the coating composition; and/or system parameters of a pressure measurement system used for acquiring the training force-displacement profiles, the system parameters being selected from a group comprising type of temperature of the coating composition, measurement probe, sensitivity of the measurement probe, length of the measurement path, speed of the measurement probe while the probe is being displaced along the measurement path, speed profile of the measurement probe while the probe is being displaced along the measurement path, and the like.

Training the predictive model to be integrated in the phase-separation-identification program on the above-mentioned context data may be advantageous, because applicant has observed that the above-mentioned context parameters may all have an impact on the number and type of phases to be observed in the coating composition and hence have an impact on the coating composition quality. Annotating the training force-displacement profiles with the above-mentioned context data and/or the quantitative measure of the phases made sure that the trained predictive model is able to take into account any factor that may have an impact on the type and extent of phases and on the quality characterizations of the coating composition.

FURTHER EMBODIMENTS

In a further aspect, the invention relates to a computer-implemented method for providing a coating-composition-related prediction program, e.g. a composition-quality-prediction program and/or a coating-composition-specification-prediction program. The method comprises:

providing a database comprising associations of qualitative and/or quantitative characterizations of coating compositions in association with one or more parameters selected from the group comprising one or more of the components of the coating composition, relative and/or absolute amounts of one or more of the said components and/or manufacturing-process parameters of the coating composition;

training a machine learning program on the associations of the coating composition characterizations with the one or more parameters in the database for providing a predictive model (M2, M3) having learned to correlate qualitative and/or quantitative characterizations of one or more coating composition with one or more of the parameters stored in association with the respective coating components and/or manufacturing-process parameters used for generating the coating composition; and providing a composition-quality-prediction program which comprises the predictive model (M2), the composition-quality-prediction program being configured for using the predictive model (M2) for predicting the properties of a coating composition from one or more input parameters selected from the group comprising one or more components of a coating composition, relative and/or absolute amounts of one or more of the said components and/or manufacturing-process parameters, the properties including the detection of a phase separation; and/or providing a composition-specification-prediction program which comprises the predictive model (M3), the composition-specification-prediction program being configured for using the predictive model (M3) for predicting, based on an input specifying at least desired storage stability characterization and optionally one or more additional parameters related to the desired coating composition (components, process parameters, application parameter) and outputting one or more parameters related to a coating composition predicted to generate a coating composition having the input storage characterizations and optionally meeting the additional parameters as input, the one or more parameters being selected from the group comprising one or more components of the said coating composition, relative and/or absolute amounts of one or more of the said components and/or manufacturing-process parameters to be used for preparing the coating composition.

Embodiments of the invention may have the advantage that a composition-quality prediction program is provided which is able to automatically predict quality characterizations of a particular coating composition as a function of the type and/or amount of the components of the composition and optionally as a function of further parameters. This may tremendously accelerate the process of testing and identifying a coating composition which is able to provide a coating composition having the desired quality characterizations. Contrary to prior art approaches which are based on human experience and a typical large number of coating compositions manufactured and tested at the workbench, embodiments of the invention may allow accurately predicting, whether or not a particular coating composition will have the desired coating composition characterizations or not. This may tremendously accelerate the process of identifying a suitable coating composition and reduce the costs associated with reagents, machines and consumables required to perform this identification process.

While the predictive model M1 of the phase-separation-identification program is preferably obtained by performing a machine learning step on manually annotated training force-displacement profiles and has learned to correlate force-displacement patterns with phase-type characterization measures and coating composition characterizations, the predictive model M2 of the composition-quality prediction program can be trained on training data which may or may not comprise force-displacement profiles. The purpose of the predictive model M2 is to predict coating composition characterizations, in particular quality-related characterizations, as a function of the one or more components and optionally also context parameters of a coating composition.

According to embodiments, the method comprises providing a plurality of force-displacement profiles respectively related to coating compositions. The coating compositions respectively having one or more phases of multiple different types. The method comprises applying a phase-separation-identification program on the force-displacement profiles for recognizing force-displacement patterns in the force-displacement profiles, for obtaining the measures of the phases represented by the identified force-displacement patterns and for computing a qualitative and/or quantitative characterization of the coating compositions represented by the force-displacement profiles. The method further comprises storing the qualitative and/or quantitative characterizations of the phases (and optionally also qualitative and/or quantitative measures of the individual phases) in association with one or more parameters related to the coating composition used for creating the coating composition comprising these phases in the database for providing the training data for the predictive model (M2, M3). For example, these parameters can be selected from the group comprising one or more of the components of the coating composition, relative and/or absolute amounts of one or more of the said components and/or manufacturing-process parameters of the coating composition.

This may be advantageous as the automated phase identification and coating composition characterization may allow to annotate a huge number of force-displacement profiles automatically in a reproducible and comparable manner. Providing a large, unbiased training data set may ensure that the model M2 having been trained on this training data set is able to predict the coating composition properties accurately.

According to embodiments, the using of the composition-quality-prediction program comprises:

providing each of the specifications of a plurality of different candidate coating compositions as input to the composition-quality-prediction program;

predicting, by the composition-quality-prediction program, for each of the candidate coating compositions the quality of a coating selecting a candidate coating composition in dependence on the respectively predicted measures; and outputting a specification of the selected candidate coating composition as a recommended coating composition predicted to have the highest quality; and/or inputting the specification of the selected candidate coating composition to a processor which controls a facility for producing and/or testing compositions for coating compositions, wherein the processor drives the facility to produce the input coating composition.

For example, the prediction is generated by a computer system connected to the facility for producing and/or testing compositions for coating compositions. The facility can be a HT-facility.

According to embodiments, the method further comprises:

receiving an incomplete specification of a coating composition;

manually or automatically generating a set of specifications of candidate coating compositions; the set of candidate compositions are different versions of the received incomplete coating composition; the creation of the specifications of the candidate coating compositions comprises:
   a) supplementing the specification of the incomplete coating composition with one or more further components; and/or
   b) supplementing the specification of the incomplete coating composition with different absolute or relative amounts of the one and/or more components or different absolute or relative amounts of the one or more further components; and/or
   c) changing the amounts of one or more components given in the incomplete coating composition; and/or
   d) supplementing the specification of the incomplete coating composition with one or more manufacturing-process-parameters characterizing the process of manufacturing the candidate coating composition.

For example, the received incomplete specification may specify that the (desired) coating composition should comprise a particular dispersing agent and a particular pigment but does not specify their absolute or relative amounts. The candidate compositions could be created such that different amount ratios of the dispersing agent and the pigment are used.

According to another example, the incomplete specification may specify that a particular pigment or pigment combination should be used but is silent about the amount of the pigment or only provides an amount range of the pigment(s). The candidate compositions could be coating compositions differing from each other in respect to the amount of the pigment(s).

According to another example, the incomplete specification may specify all or at least most of the components of the coating composition and their respective amounts but is silent about context parameters, in particular manufacturing process parameters such as mixing time, mixing duration, mixing temperature etc. The candidate compositions could be coating compositions differing from each other in respect to the parameter values of one or more of the above-mentioned context parameters.

According to another example, incomplete specification may specify all or at least most of the components of the coating composition and their respective amounts but is silent about its phase separation properties. The candidate compositions could be coating compositions differing from each other in respect of different amount of rheological modifier(s) or of different type of rheological modifier(s).

According to embodiments, the further data used for supplementing the candidate coating composition specifications in the respective cases a), b), c) and/or d) is used as input by the coating composition-quality-prediction program for performing the prediction.

The above described embodiments are based on providing a plurality of (hypothetical) candidate coating composition specifications, predicting the respective coating quality and selecting the one of the candidate coating compositions whose predicted properties appear to be most desirable. However, alternative approaches may use the learned correlations between the coating storage stability characteristics and the coating composition related parameters which have been incorporated in the predictive model M3 more directly for identifying promising coating compositions.

According to embodiments, the using of the coating composition-specification-prediction program comprises providing a composition-specification-prediction program which comprises the predictive model (M3), the composition-specification-prediction program being configured for using the predictive model (M3) for predicting, based on an input specifying at least desired storage stability characterization and optionally one or more additional parameters related to the desired coating composition (components, process parameters, application parameter) and outputting one or more parameters related to a coating composition predicted to generate a coating composition having the input storage characterizations and optionally meeting the additional parameters as input, the one or more parameters being selected from the group comprising one or more components of the said coating composition, relative and/or absolute amounts of one or more of the said components and/or manufacturing-process parameters to be used for preparing the coating composition.

According to preferred embodiments, the method further comprises outputting the predicted specification of the coating composition to a human and/or inputting the specification of the selected candidate coating composition to a processor which controls a facility for producing and/or testing compositions for coating compositions, wherein the processor drives the facility to produce the input coating composition.

In addition to the desired storage stability, additional constraints may be provided as input. The constraints may consist of an incomplete, rough coating composition specification being indicative of some components or component substance classes and some absolute or relative amounts. The constraint may be that any alternative component suggested must belong to the same substance class or any alternative amount must not deviate from the amount provided in the constraint by more than a maximum threshold value. Manufacturing process parameters and/or application process parameters may also be provided as constraints.

According to embodiments, the method is performed on a computer system operatively coupled to an automated receptacle receiving and force measuring acquisition unit (RRFMA unit). The RRFMA unit comprises a measurement probe The RRFMA unit is a component of a facility for producing and/or testing coating compositions or is operatively coupled to the facility by automated transport means, e.g. for automatically transporting a coated surface sample to and from the RRFMA unit. The method further comprises sending one or more control commands to the facility. The control commands cause the facility to:

transport the produced coating composition to the RRFMA unit;

positioning of the measurement probe relative to, in particular above, the coating composition in the receptacle;

controlling the measurement instrument to displace the measurement probe through the coating composition along a predefined measurement path with a predefined speed profile, the predefined measurement path extending along a length axis of the receptacle, causing the measurement probe for acquiring a force-displacement profile, while displacing of the measurement probe through the coating composition, by measuring a force exercised on the measurement probe while the probe is being displaced along the predefined measurement path with the predefined speed profile; and returning the acquired force-displacement profile to the computer system.

This may be advantageous as a fully automated system for predicting, manufacturing, and testing a coating composition in the context of an automated manufacturing facility, in particular a HT-facility, is provided. The data obtained in the force-displacement profile-analysis based testing step may be used for extending the training data of the composition-quality-prediction-program, and for re-training the model M2 of the composition-quality-prediction-program on the extended training data for obtaining an improved version of the model M2.

According to embodiments, active learning is used during the training of the predictive model M1 to be used for identifying force-displacement patterns and thereby phases in force-displacement profiles of coating compositions. In this case, the active learner identifies a subset of one or more of a plurality of unlabeled test force-displacement profiles of coating compositions whose manual annotation would provide the highest learning effect. The active learning module prompts a user to manually annotate (assign labels) to each force-displacement profile of the subset, whereby the label indicates type and location of the phases depicted therein. These one or more additionally labeled force-displacement profiles are added to the training force-displacement profiles, thereby extending the training data. The predictive model M1 is re-trained on the extended training data, thereby providing an improved, more accurate version of the predictive model M1. Then, the outdated predictive model in the phase-separation-identification program is replaced by the improved version of the model.

In a further aspect, the invention relates to a system comprising:
- a facility for producing and testing compositions for paints, varnishes, printing inks, grinding resins, pigment concentrates or other coating materials, where the facility comprises at least two workstations, where the at least two workstations are connected to one another via a transport system on which self-propelled transport vehicles are able to run for transporting the components of the composition and/or of the composition produced between the workstations, and
- a computer system configured to perform the method of any one of the embodiments described herein.

In a further aspect, the invention relates to a computer program configured to perform the method of any one of the embodiments described herein. The computer program may be a computer program product.

In a further aspect, the invention relates to a phase-separation-identification program provided by performing a method of providing and using the phase-separation-identification program as described herein for embodiments of the invention.

In a further aspect, the invention relates to a composition-quality prediction program provided by performing a method of providing and using the composition-quality prediction program as described herein for embodiments of the invention.

In a further aspect, the invention relates to a composition-specification-prediction program provided by performing a method of providing and using the composition-specification-prediction program as described herein for embodiments of the invention.

In a further aspect, the invention relates to a coating-composition manufactured in accordance with a specification of a composition provided by performing a method of any one of the embodiments for providing a specification of a coating composition described herein. In particular, the specification can be computed according to embodiments of the invention by the coating-composition-specification-prediction program or the composition-quality-prediction program based on a respective desired storage stability characterization provided as input using a trained model (e.g. M2 or M3).

In a further aspect, the invention relates to a volatile or non-volatile data storage medium comprising computer-interpretable instructions implementing the phase-separation-identification program, the composition-quality-prediction program and/or the composition-specification-prediction program.

In a further aspect, the invention relates to a volatile or non-volatile data storage medium comprising the above-mentioned specification, the data storage medium being operatively coupled via an interface to a facility, the facility being configured for producing coating compositions in accordance with one or more specifications stored in the data storage medium.

In a further aspect, the invention relates to a measurement instrument for acquiring a force-displacement profile by measuring a force exercised on a measurement probe while the probe is being displaced through the coating composition along a predefined measurement path with a predefined speed profile, the measurement instrument being configured to carry out a method as described herein for embodiments of the invention.

The term "composition" or "coating composition" as used herein is a product which comprises two or more raw materials ('components') from which the product is formed. When in the context of this application reference is made to the production or testing of a composition by an automated facility, this is to be understood that the product is produced according to information on the nature and/or amount of the components.

A "coating surface" as used herein is a surface of a substrate having been coated one or multiple times with a coating composition. For example, the coating composition can be applied by spreading or spraying or painting the coating composition onto the substrate, by immersing at least one surface of the substrate in the coating composition, or by other coating approaches.

A "program" as used herein is a piece of software, e.g. an application program or a module or function of an application program, or a script, or any other kind of code that is executable by one or more processors, e.g. CPUs or GPUs.

A "phase-separation-identification program" as used herein is a software program or software module configured to analyze force-displacement profiles for automatically identifying one or more phases and for computing a coating composition characterization as a function of the identified phases depicted in the force-displacement profile.

A "force-displacement profile" depicts multiple recorded forces exercised on a measurement probe while the measurement probe is being displaced through a coating composition along a predefined measurement path with a predefined speed profile. The multiple recorded measured forces may be visualized as a curve in a diagram.

A "composition-quality prediction program" as used herein is a software program or software module configured to receive a (complete or incomplete) specification of a coating composition and is configured to predict one or more properties of the coating composition as a function of the data specified in the specification. The properties of the coating composition can comprise an indication of the quality of the coating composition, e.g. an indication of the quality of the storage stability of the coating composition. The quality indication may be, for example, the likelihood of generating certain types of phases.

A "composition-specification prediction program" as used herein is a software program or software module configured to receive a desired storage stability characterization as input parameter(s). Optionally, the composition-specification prediction program can be configured to receive one or more further input parameters such as an incomplete specification of a coating composition for limiting the solution space of the prediction. The composition-specification prediction program is configured to predict one or more of the following output parameters as a function of the received input data: one or more components, one or more absolute or relative component amounts, one or more manufacturing process parameters and/or one or more application process parameters.

A "specification of a composition" as used herein is a data set comprising parameters related to a coating composition. For example, the parameters can indicate the identity and/or substance class of some or all components to be combined for manufacturing a coating composition. Optionally, the specification may comprise additional parameters, e.g. the relative or absolute amounts or amount ranges of the respective components, coating composition manufacturing process parameters, and the like. These parameters may specify how the components have to be processed and/or mixed for obtaining the composition and/or how the composition is to be applied on a substrate to obtain a particular coating surface. The specification of a composition may be complete or incomplete. For example, some specifications may only indicate the type of a component but not the exact identity and/or amount of the component. The "specification" of a composition may be provided in various forms, e.g. as printout, as file, e.g. an XML file, an object of an object-oriented programming language, as JSON file or the like.

A "coating composition manufacturing process parameter" or "manufacturing process parameter" as used herein is a parameter being indicative of properties of a process of processing and/or combining the components to form a composition. Examples are mixing duration, mixing speed, mixing temperature, sequence of mixing components, devices used for mixing or otherwise preparing the coating composition or the like.

A "known composition" as used herein is a composition that specifies a product whose properties (e.g. rheological properties, elasticity, shelf-life etc.) are known at the time of training of a neural network to the person or organization conducting the training. For example, the known composition may have been used to produce a product for a customer several months or years ago and the properties of that product have been measured empirically. The measurement does not necessarily have to have been carried out by the operator of the laboratory which now determines the predictive composition, but may also have been carried out and published by other laboratories, so that in this case the properties are taken from the specialist literature. Since a composition according to the above definition also contains formulations as a subset, the "known compositions" according to the embodiments of the invention may also contain "known formulations" or be "known formulations".

A "database" as used herein is any volatile or non-volatile data storage medium in which data, in particular structured data, is stored. The database can be one or more text files, spreadsheet files, a directory in a directory tree, or a database of a relational database management system (DBMS) such as MySQL or PostgreSQL.

A "loss function" of a prediction problem as used herein is a function that is used in the training of a predictive model (e.g. a model of a neural network) by a machine learning program for training and improving the model. The loss function outputs a value whose magnitude gives an indication of the quality of the predictive model, whereby the loss function is minimized in the course of the training, since the magnitude of this value indicates the inaccuracy of the predictions of the predictive model.

A "facility" for the production and testing of compositions as used herein is an apparatus or system comprising several laboratory devices and a transport unit, which is capable of jointly controlling the laboratory devices and the transport unit in an orchestrated manner in order to carry out a workflow automatically or semi-automatically. The workflow can be, for example, a coating composition preparation workflow (e.g. a combine-and-mix workflow), or an analysis workflow or a combination of two or more of these workflows. The workflow can comprise automatically preparing a coating composition and/or automatically storing the coating composition and/or automatically recording the force-displacement profile and/or applying the composition on one or more substrates. The facility can be, for example, a high-throughput facility (HT-facility), also referred to as "high-throughput equipment" (HTE).

The "testing" or "analysis" of a coating composition by an automated manufacturing and/or testing facility is the process of analyzing chemical, physical, mechanical, optical or other empirically measurable properties of the composition by means of one or more analysis modules. For example, the testing may comprise acquiring and analyzing a force-displacement profile of the coating composition, and computing a quality measure of the coating as a function of one or more phases detected in the coating composition. The analysis may further comprise measuring further object properties, e.g. opaqueness, elasticity, rheological properties, color, etc.

An "active learning module" as used herein is a software program or a module of a software program which is designed to select a (comparatively small) subset of test compositions from a set of test compositions in such a way that a particularly strong learning effect occurs after preparation and empirical measurement of the properties of this selected test composition as a consequence of the consideration of these data in training the predictive model.

A "model" or "predictive model" as used herein is a data structure or executable software program or program module configured to generate a prediction based on input data. For example, the model can be a model obtained in a machine-learning process by training the model on manually and/or automatically annotated training data. The predictive model can be, for example, a neural network model, a support vector model, a random forest, a decision tree, or the like. According to embodiments of the invention a predictive model adapted to compute a characterization of a coating composition in respect to the presence, location and/or extent of one or more phases based on acquired force-displacement-profile is also referred to as "M1" model. A predictive model adapted to predict a property of a coating composition based on one or more input parameters related to e.g. the components, component amounts and/or manufacturing process parameters application process parameters of this composition is also referred to as "M2" model. A predictive model adapted to predict on one or more parameters related to e.g. the components, component amounts and/or manufacturing process parameters of a coating composition based on input data specifying a desired property of a coating composition, is also referred to as "M3" model.

BRIEF DESCRIPTION OF THE DRAWINGS

In the following, only exemplary forms of the invention are explained in more detail, whereby reference is made to the drawings in which they are contained. They show.

DETAILED DESCRIPTION

Figure 1A:
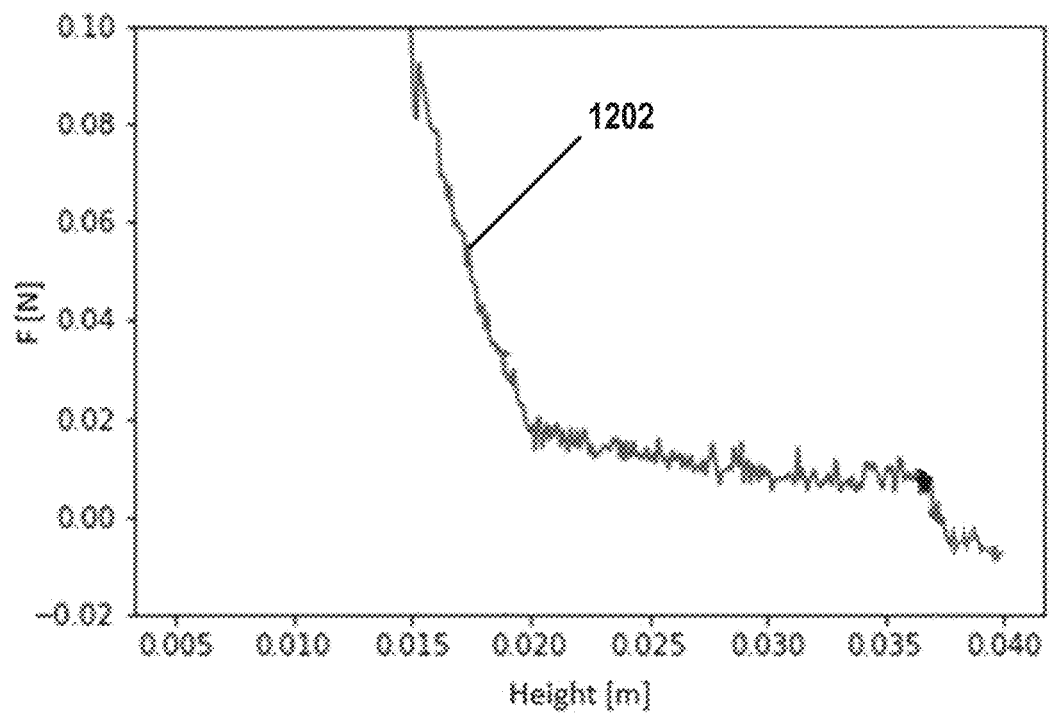
FIG. 1A a force-displacement profile (curve) of a coating composition

FIG. 1A shows a sub-area of an acquired force-displacement profile 1202 of a coating composition.

For example, the force-displacement profile may have been acquired by a measurement probe in a force-displacement profile acquisition unit of a facility for automatically manufacturing and/or testing coating compositions. Alternatively, the force-displacement profile may have been obtained by a measurement probe of a data processing system described for example with reference to FIGS. 6B to 6C.

The acquisition of the force-displacement profile 1202 shown in FIG. 1A was performed with a measuring head DSR 301 with the measuring probe PP 25. The sample was fixed in a 100 ml glass receptacle on a shuttle. The fill level of the composition within the receptacle (glass) may vary. The measuring probe was moved centrally into the sample and the force required to move the sample was measured. The parameters start height [mm], end height [mm] and speed [mm/s] may be varied. A common parameter set is 400 mm initial height, 5 mm final height and 1 mm/s speed.

The recorded force-displacement profile 1202 may be used to illustrate the phase-separation detection. Since the measuring probe is moved into the sample from above, the course of the measurement in the diagram is from right to left (decreasing height).

In order to generate a training data set of sufficient size, force-displacement profiles of many different coating compositions comprising many different types of phases are acquired.

Preferably, a large number (e.g. several thousand) of force-displacement profiles showing different phase types are acquired, which may be manually annotated (labeled).

Figure 1B:
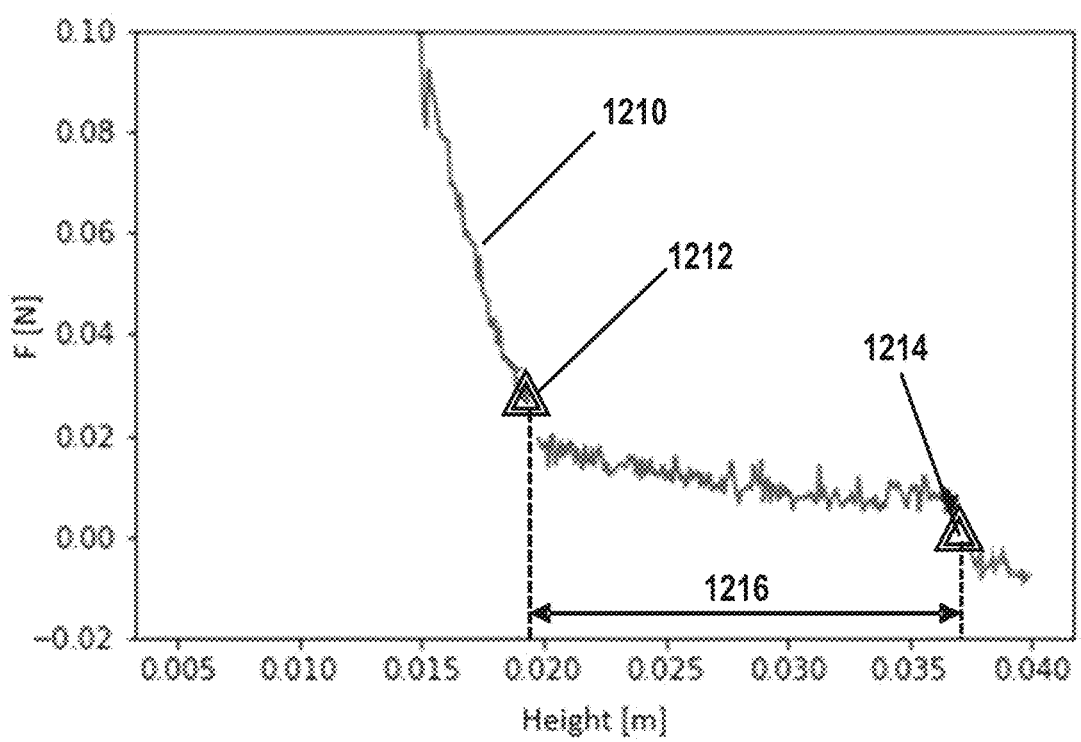
FIG. 1B the force-displacement profile of FIG. 1A showing the threshold values (boundaries) of phases.

FIG. 1B shows the force-displacement profile 1202 of FIG. 1A comprising determined boundaries of a phase (force-displacement patterns) 1212, 1214. The force-displacement patterns 1212 and 1214 have been automatically marked with triangles, using a thresholding operation, each indicating an identified force-displacement pattern.

For example, phase separation of the coating composition may be detected from the shown force-displacement profile. The height of the measuring probe in a receptacle, whereby the measurement probe is displaced through the coating composition along a predefined measurement path with a predefined speed profile, is shown on the X-axis and the measured/recorded force is shown on the Y-axis. As the height of the measurement probe was decreased during the measurement, the course of the measurement is from right to left in the diagram. The detection was performed using the following steps:

Calculating the average of the recorded force for the first section of the measurement. The first section comprises the measurements of the force recorded from the start of the measurement to the first force-displacement pattern 1214 or the first increase in the force-displacement profile. In the first section the measuring probe is not yet immersed in the coating composition sample and the measurement is performed in air. Therefore, only the background noise is measured.

Shifting the recorded force-displacement profile (curve) by the previously calculated average value. Therefore, the noise may be around zero on the Y-axis.

Determining the end of the first phase (force-displacement pattern 1212 in the diagram). The end of the first phase is defined as the first measuring point at which the force exceeds a determined first threshold value (e.g. 0.03 N).

Determining the beginning of the first phase using the recorded force-displacement profile (curve), starting from the end of the first phase going backwards to the beginning of the measurement. The beginning of the first phase (force-displacement pattern 1214 in the diagram) is defined as the first measuring point in this direction at which the force falls below a determined second threshold value (e.g. 0.002 N)

The length of the phase is calculated from the difference of the X-values (1216) of these two threshold values (force-displacement patterns 1212 and 1214).

Figure 2:
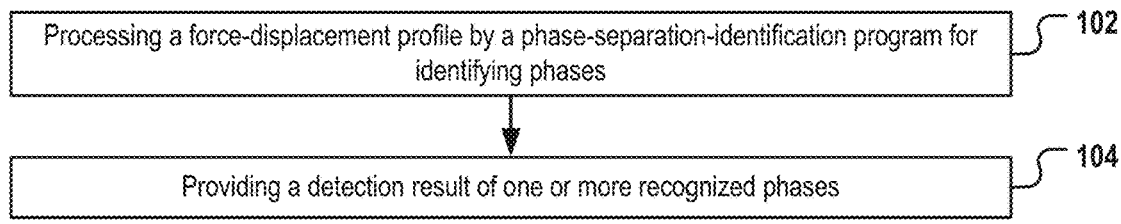
FIG. 2 a flowchart of a method for automated characterization of a coating composition.

FIG. 2 shows a flowchart of a method for detecting a phase separation of a waterborne or solvent-borne or solvent-free coating composition. In a first step 102, a phase-separation-identification program processes a force-displacement profile recorded for a coating composition. The phase-separation-identification program identifies one or more phases and provides a characterization of the recognized phases in step 102. For example, the program may determine that the coating composition comprises two phases. The characterization of the recognized phase may comprise the type, location and extent of the identified phase. The data obtained in step 104 may be output to a user and/or may be used internally by the phase-separation-identification program for computing derivative data values, e.g. aggregated coating composition characterizations.

Figure 3:
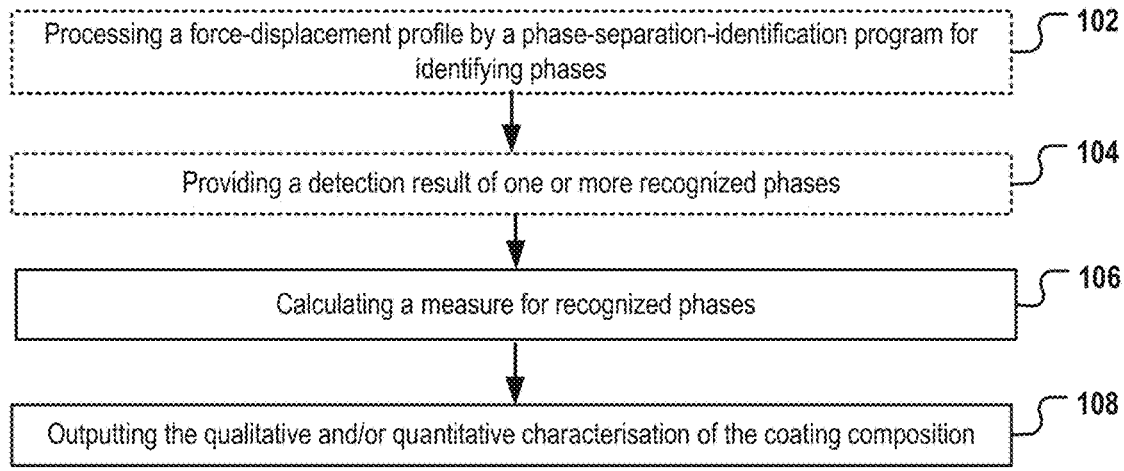
FIG. 3 a flowchart of a method for automated characterization of a coating composition in greater detail.

FIG. 3 shows a flowchart of a method for automated characterization of a coating composition in greater detail. After steps 102 and 104, the phase-separation-identification program in step 106 computes measures of the individual phases, e.g. volume, phase location or the like. The phaseseparation-identification program uses these measures in steps 106 and 108 to compute and provide a qualitative and/or quantitative characterization of the coating composition.

Figure 4:
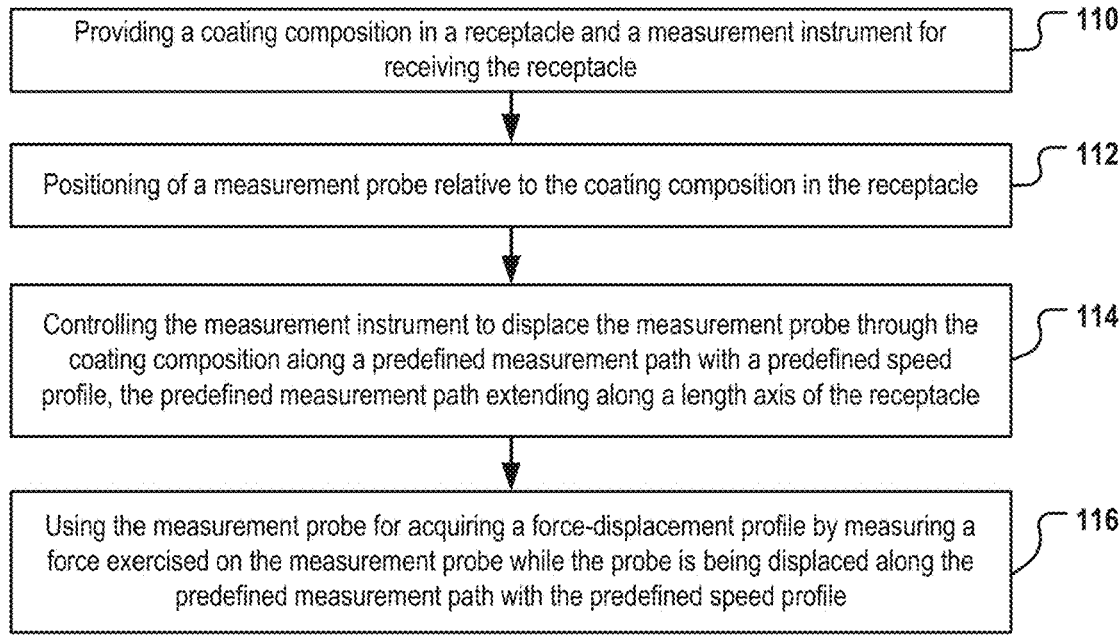
FIG. 4 a flowchart of a method for obtaining a force-displacement profile.

FIG. 4 shows a flowchart of a method for obtaining a force-displacement profile of a waterborne or solvent-borne or solvent-free coating composition. Before step 110, a plurality of coating compositions may be generated by mixing multiple components with each other according to a mixing and manufacturing protocol. In step 110 a coating composition is provided in a receptacle. Further, a measurement instrument for receiving the receptacle is provided, the measurement instrument comprising a measurement probe. The samples are transported automatically or manually to a force measuring acquisition unit. In step 112, the measurement probe is positioned relative to the coating composition in the receptacle. In steps 114 and 116, a measurement probe is displaced through the coating composition in a defined manner as to enable a force-displacement profile analysis software 124 to correctly analyze the force-displacement profiles. Hereby, one or more force-displacement profiles depicting phases are acquired.

Figure 5:
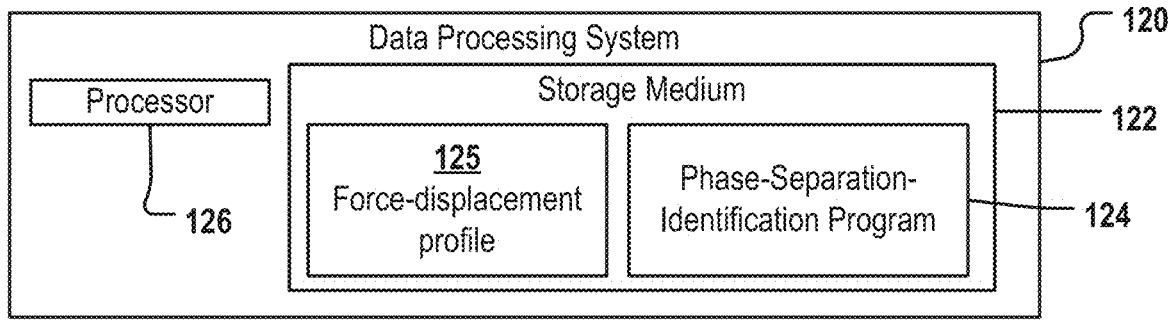
FIG. 5 a block diagram of a data processing system for automated surface coating characterization.

FIG. 5 shows a block diagram of a data processing system 120 for automated coating characterization. The data processing system comprises one or more processors 126 and a volatile or nonvolatile storage medium 122. The storage medium can comprise force-displacement profiles 125, e.g. training force-displacement profiles for training the model M1 of the phase-separation-identification program 124 or test force-displacement profiles to be input to the already trained predictive model M1. In addition, or alternatively, the storage medium can comprise training data for training the model M2 of the composition-quality prediction program and/or can comprise the composition-quality prediction program comprising an already trained predictive model M2.

The data processing system 120 can be implemented in many different ways. For example, the data processing system can be a monolithic computer system, e.g. a desktop computer system, a portable telecommunication device, a smart phone, a special purpose coating composition-quality control device or a computer system being operatively coupled to or being an integral part of a facility for automatically manufacturing and/or testing coating compositions. Alternatively, the data processing system 120 can be a distributed computer system, e.g. a client/server computer system optionally coupled to one or more facilities for automated manufacturing and/or testing of coating compositions. The components of the distributed computer system can be communicatively linked with each other via a network connection, e.g. the Internet or an intranet of an organization. FIGS. 5A-5D illustrate some implementation examples of the data processing system 120.

Figure 6A:
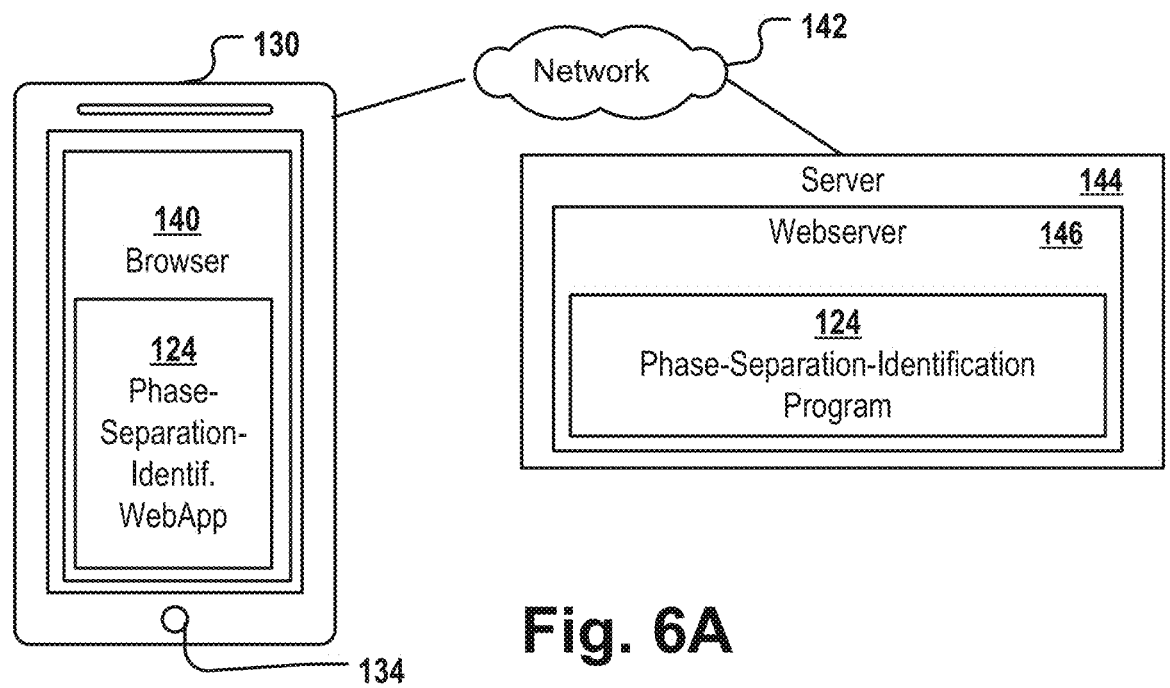
FIG. 6A a data processing system in the form of a smart phone comprising a web-application.

FIG. 6A shows a data processing system in the form of a smart phone 130 comprising the phase-separation-identification program 124 in the form of a web-application.

According to one example, the phase-separation-identification program is implemented as a script that runs in the browser of the smartphone and that is downloaded by a user visiting a particular website, e.g. a web portal of a company generated by a server 144 and offered via the Internet or intranet. For example, the program 124 can be implemented as JavaScript program.

According to another embodiment, the phase-separation-identification program is implemented as a program running outside of a browser, e.g. a Java program.

The phase-separation-identification program can be implemented as a two-component program comprising a client portion and a server portion which are interoperable and are configured to exchange data via a network connection 142. For example, the program portion installed on the portable telecommunication device 130 ("client application") can be configured to controlling the force-displacement profile acquisition process and for outputting the phase-separation identification results to a user. The program portion installed on the server ("server application") can be configured to receive the force-displacement profile from the client portion via the network, to analyze the force-displacement profiles for detecting phases, for determining measures of the identified phases and for computing a qualitative and/or quantitative characterization of the coating composition. The server portion returns the characterization and preferably also the measures and an indication of the type and extend of the identified phases to the client portion.

Figure 6B:
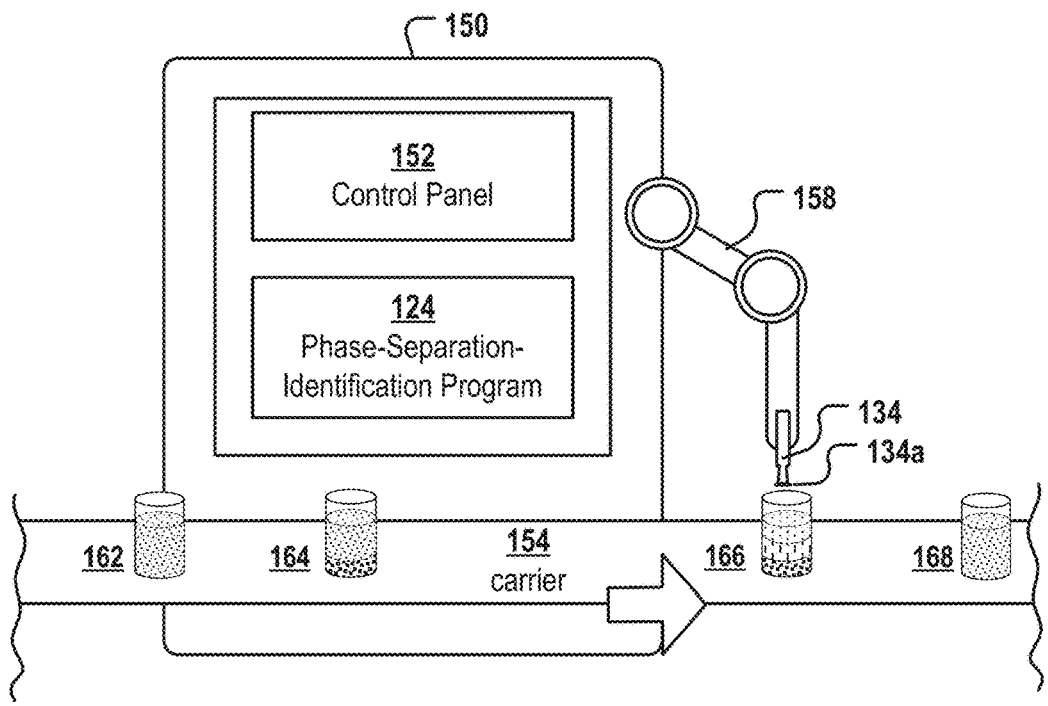
FIG. 6B a data processing system in the form of a customized phase identification quality control device.

FIG. 6B shows a data processing system 150 in the form of a customized surface coating quality control device, i.e., a dedicated hardware designed for controlling and objectivizing the quality of coating compositions and, implicitly, the quality of the coating generation process. The device comprises a storage medium with the phase-separation-identification program 124, an interface 152 allowing a user to control the quality control and testing process, and preferably several hardware components used for the purpose of testing the composition properties of composition samples. For example, the device can comprise a measurement probe 134 coupled to the device via a robotic arm 158 or via other connecting elements which allow to modify the relative position of measurement probe and receptacle with the coating composition or vice versa. The measuring probe 134 comprises a contact surface 134a on which the dynamic pressure of the coating composition, through which the measuring probe is moved, is exercised, thereby acting a force on the holder of the contact surface 134a, wherein this force acting on the holder of the contact surface 134a is proportional to the dynamic pressure of the coating composition.

The control device 150 can be implemented as portable device or as stationary device. For example, the device can be implemented as an integral part of a facility for automatically manufacturing and/or testing coating compositions. The facility comprises a conveyor belt 154 for transporting a plurality of composition samples 162, 164, 166, 168 to the control device 150, thereby enabling a fully automated, fast and reproducible quality control of many coating compositions. As indicated, the composition samples 162, 164, 166, 168 may comprise various coating compositions, which thus may result in different phase separations. As shown, the composition samples 162 and 168 do not comprise any phase-separations, the composition sample 164 comprises two phases and the composition sample 166 comprises three phases.

Figure 6C:
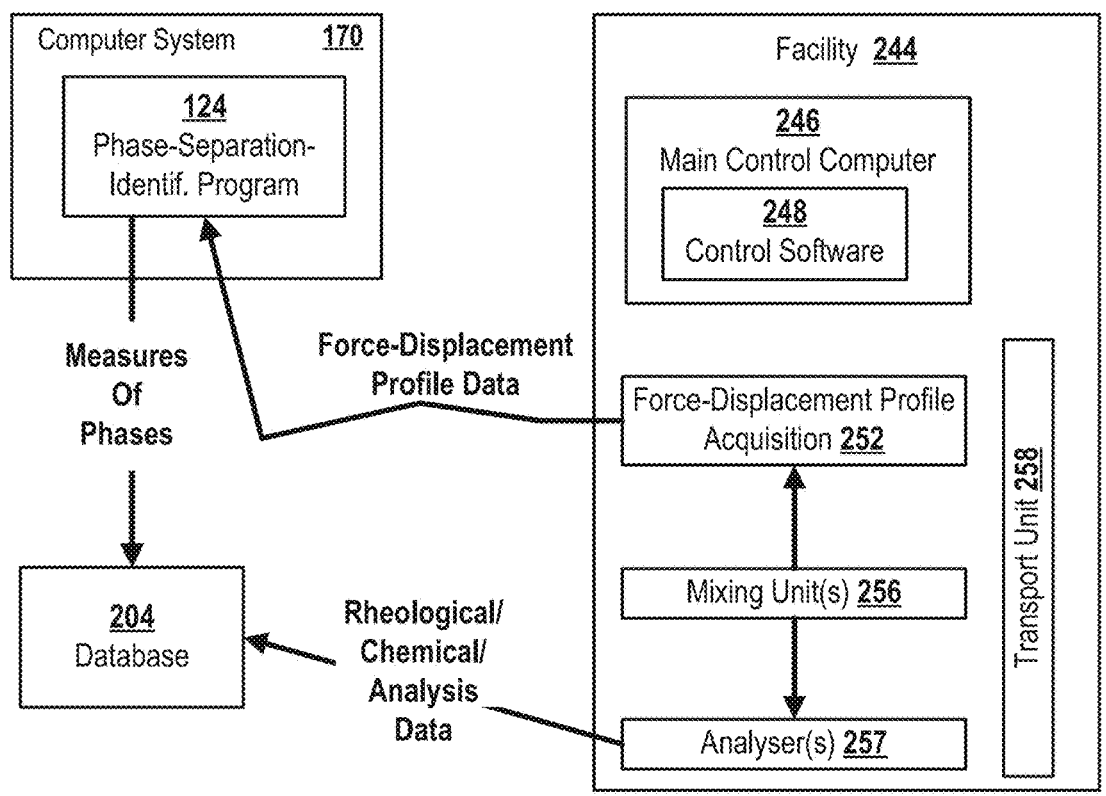
FIG. 6C a data processing system in the form of a computer coupled to a facility for manufacturing coating compositions.

FIG. 6C shows a data processing system in the form of a computer 170 coupled to a facility 244 for manufacturing coating compositions.

The facility 244 comprises a main control computer 246 for controlling, monitoring and/or orchestrating various tasks related to the manufacturing of coating compositions, related to the application of coating compositions on various surfaces and/or related to the testing of the coated surfaces or of the coating compositions (e.g. for determining rheological, chemical, physical or other parameters of the coating composition). The respective tasks are performed by several different units comprised by the facility 244. For example, the facility can comprise one or more analyzers 257 for performing chemical, physical, mechanical, optical or other forms of tests and analysis. The facility can comprise one or more mixing units 256 configured for manufacturing various coating compositions, e.g. by mixing the components of a composition based on a specific manufacturing and mixing protocol. According to some example implementations, the facility further comprises an force-displacement profile acquisition unit 252 comprising a measurement probe and means for positioning the sample and the measurement probe relative to each other such that the acquired force-displacement profiles can be used as input by the phase-separation-identification program 124. One or more transport units 258, e.g. conveyor belts, connect the different units and carry components, mixtures and coating compositions from one unit to the other.

The control computer 246 comprises a control unit 248 configured for sending the force-displacement profiles of composition samples acquired in the force-displacement profile acquisition unit 252 to the phase-separation-identification program 124 of computer system 170. Preferably, additional data, e.g. a complete or incomplete specification of the components of the coating composition, and optionally also information on the manufacturing process of the coating composition, are provided together with the force-displacement profile data to the phase-separation-identification program. The phase-separation-identification program is configured to use the received force-displacement profile, and optionally also the additional data, as input for automatically identifying phases depicted in the force-displacement profile, for computing measures and for computing coating composition characterizations as the function of the phase measures. The results computed by the phase-separation-identification program can be output to a user via a GUI and/or can be stored in the database 204.

Preferably, parts of the data obtained by the other units such as the analyzers 257 or the mixing units 256 can be storage directly in the database in association with an identifier of a particular coating composition and/or coated samples or can be sent to the computer system 170 to have the computer system 170 store the data in the database.

Using the phase-separation-identification program in the context of the facility 244 can be particularly advantageous, because after the force-displacement profiles of the coating compositions have been taken, they can be automatically analyzed for the phases to be examined. The result obtained can be linked to the formulation data and/or analysis data and thus be used to optimize the composition.

Figure 7:
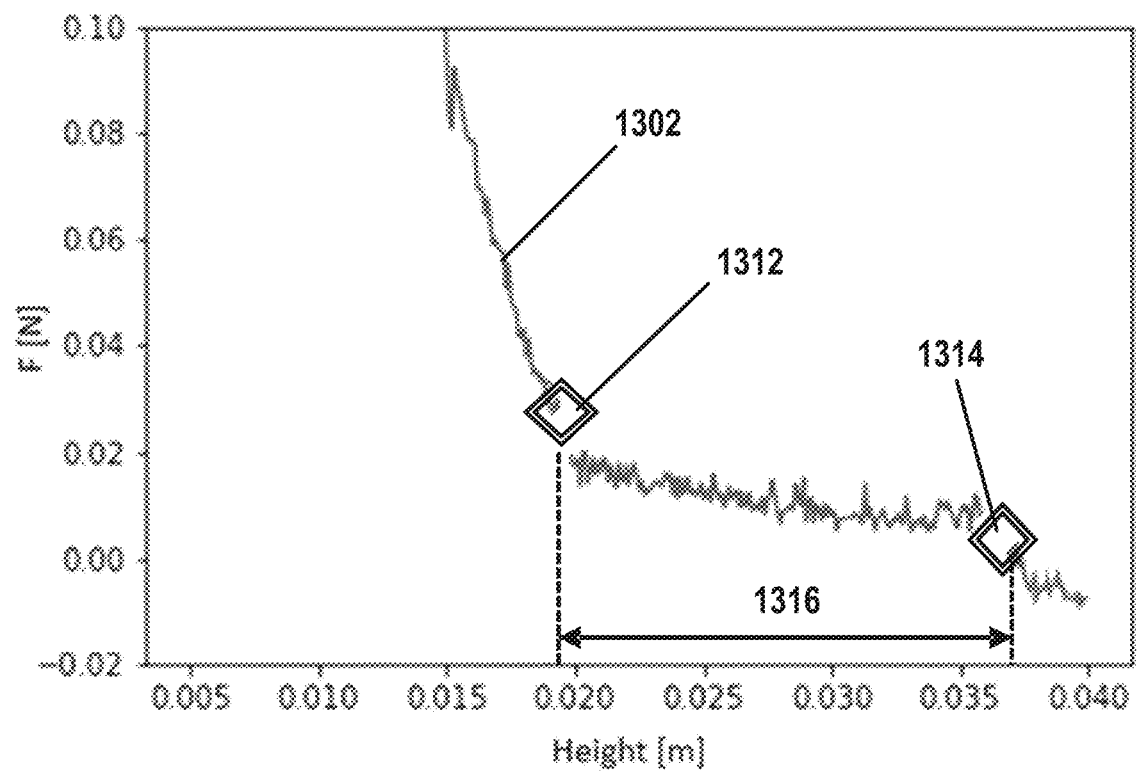
FIG. 7 a force-displacement profile of a coating composition with automatically identified and labeled force-displacement patterns, each force-displacement pattern being assigned to the boundary of a type of phase.

FIG. 7 shows a force-displacement profile 1302. The force-displacement profile comprises labels 1312, 1314 which have been automatically created by a phase-separation-identification program 124 according to an embodiment of the invention. The labels represent force-displacement patterns 1312, 1314 having been automatically detected by the phase-separation-identification program. Further, e.g. a length of the phase (and thereby the amount/volume of the phase) may be calculated from the difference of the X-values (1316) of these two force-displacement patterns (1312, 1314).

In addition to the visual representation of the detected force-displacement patterns, the phase-separation-identification program is configured to temporarily or permanently store the types and locations of the identified phases also in a structured form. For example, the location can be stored in the form of pattern coordinates of two force-displacement patterns representing a phase. Storing the identity and location of the phases in structured form allows the phase-separation-identification program to process the structured data to compute aggregated characterizations of the coating composition.

LIST OF REFERENCE NUMERALS

102-116 steps
120 data processing system
122 data storage medium
124 phase-separation-identification program
125 force-displacement profile
126 processor(s)
130 portable telecommunication device
134 measurement probe
134a contact surface of measurement probe
140 browser
142 network
144 server computer
146 webserver
150 coating quality control device
152 control panel
154 carrier/transportation belt
158 robotic arm
162-168 samples
170 computer system
204 database
244 facility for manufacturing and/or testing coating compositions
246 main control computer
248 control unit
252 force-displacement profile acquisition unit
256 mixing units
257 analyzers
258 transport unit
1202 force-displacement profile of coating composition
1210 labeled force-displacement profile 1202
1212 added label
1214 added label
1216 length difference of the X-values of labels 1212 and 1214
1302 force-displacement profile of coating composition
1312 automatically generated label of computationally identified pattern
1314 automatically generated label of computationally identified pattern
1316 length difference of the X-values of automatically generated labels of computationally identified patterns 1312 and 1314

The invention claimed is:

1. A method for detecting a phase separation of a water-borne or solvent-borne or solvent-free coating composition comprising
providing the coating composition in a receptacle;
providing a measurement instrument for receiving the receptacle, the measurement instrument comprising a measurement probe;
controlling the measurement instrument to
a) displace the measurement probe through the coating composition along a predefined measurement path with a predefined speed profile, the predefined measurement path extending along a length axis of the receptacle,
b) acquiring a force-displacement profile by measuring a force exercised on the measurement probe while the probe is being displaced along the predefined measurement path with the predefined speed profile;

processing the force-displacement profile for detecting at least one phase separation of the coating composition; and outputting a detection result.

2. The method of claim 1, wherein the processing of the force-displacement profile comprises a thresholding operation, a change point detection, a knee/elbow point detection, and/or the application of the Ramer-Douglas-Peucker algorithm (RDP) or isolation forest for detecting the phase separations.

3. The method of claim 2, the phase separations comprising at least two phases, a first phase and a second phase, wherein the second phase contains more fillers and/or pigments than the first phase.

4. The method of claim 3, the second phase comprising a sediment sub-phase and a filler and/or pigments-containing liquid sub-phase, further comprising
aborting the acquisition of the force-displacement profile when the measured force reaches or surpasses a predefined limit, the displacement of the probe when the predefined limit is reached being indicative of the commencement of the sediment sub-phase.

5. The method of claim 2, further comprising:
calculating a measure for the recognized phases for providing a qualitative and/or quantitative characterization of the coating composition, in particular the measure being
a quantitative measure selected from a group comprising: the length of the measurement path between two detected phase boundaries, the travelling time of the measurement probe between two detected phase boundaries, the relative sizes of the detected phases, the number of detected phases; and/or
a qualitative measure, the qualitative measure being in particular the type of the phase selected from a group comprising a gas phase, a first phase, and a second phase, wherein optionally the second phase contains more fillers and/or pigments than the first phase and/or optionally the second phase comprises a filler and/or pigments-containing liquid sub-phase and a sediment sub-phase; and
outputting the qualitative and/or quantitative characterization of the coating composition.

6. A method for detecting a phase separation of a waterborne or solvent-borne or solvent-free coating composition, the method comprising:
processing a force-displacement profile by a phase-separation-identification program, the phase-separation-identification program being configured to recognize force-displacement patterns, each force-displacement pattern being assigned to a boundary of a type of phase; and
providing a detection result of one or more phases recognized by the phase-separation-identification program.

7. The method of claim 6, comprising:
calculating, by the phase-separation-identification program, a measure for the recognized phases for providing a qualitative and/or quantitative characterization of the coating composition; and
outputting the qualitative and/or quantitative characterization of the coating composition.

8. The method of claim 7,
the measure being a quantitative measure selected from a group comprising the length of the measurement path between two detected force-displacement patterns, the travelling time of the measurement probe between two detected force-displacement patterns, the relative sizes of the detected phases, the number of detected force-displacement patterns; and/or
the measure being a qualitative measure, the qualitative measure being in particular the type of the phase selected from a group comprising a gas phase, a first liquid phase, and a second liquid phase, wherein optionally the second liquid phase contains more fillers and/or pigments than the first liquid phase and/or optionally the second liquid phase comprises a filler and/or pigments-containing liquid sub-phase and a sediment sub-phase.

9. The method of claim 6, further comprising:
providing a waterborne or solvent-borne or solvent-free coating composition in a receptacle;
providing a measurement instrument for receiving the receptacle, the measurement instrument comprising a measurement probe;
positioning of the measurement probe relative to, in particular above, the coating composition in the receptacle;
controlling the measurement instrument to displace the measurement probe through the coating composition along a predefined measurement path with a predefined speed profile, the predefined measurement path extending along a length axis of the receptacle,
while displacing of the measurement probe through the coating composition, using the measurement probe for acquiring a force-displacement profile by measuring a force exercised on the measurement probe while the probe is being displaced along the predefined measurement path with the predefined speed profile.

10. The method of claim 6, the processing of the force-displacement profile further comprising:
performing, by the phase-separation-identification program, a method comprising a thresholding operation, change point detection, isolation forest, knee/elbow detection, and/or the Ramer-Douglas-Peucker algorithm (RDP), on the force-displacement profile, thereby automatically labeling force-displacement patterns to the type of phase and the instance of this type of phase in the force-displacement profile; and
outputting the one or more identified phase instances.

11. The method of claim 6, the phase-separation-identification program comprising a predictive model (M1) having learned from training data in a training step using a machine learning program to recognize the predefined patterns, the machine learning program being in particular a neural network, optionally the method further comprises
performing the training step on the training data, the training data comprising a set of labeled digital training force-displacement profiles of coating compositions, the labels identifying the location/positions and type of phases in the training force-displacement profiles, the predictive model being trained for recognizing the pattern by means of the labeled training force-displacement profiles using back propagation.

12. The method of claim 11, wherein each of the training force-displacement profiles has assigned additional data being processed in the training step for enabling the predictive model to correlate the additional data with the phases, the additional data comprising context data, the context data comprising:
one or more components of the coating used for generating the coating composition for which the training force-displacement profile has been acquired, e.g. the type and/or amount of dispersion agent and/or the type or amount of a rheology modifier and/or the type or amount of one or more pigments and/or the type and amount of solvent; and/or one or more manufacturing-process parameters, the manufacturing-process parameters characterizing a process of generating a coating composition, the process parameters for example comprising mixing speed and/or mixing duration of the coating composition; and/or system parameters of a pressure measurement system used for acquiring the training force-displacement profiles, the system parameters being selected from a group comprising type of temperature of the coating composition, measurement probe, sensitivity of the measurement probe, length of the measurement path, speed of the measurement probe while the probe is being displaced along the measurement path, speed profile of the measurement probe while the probe is being displaced along the measurement path.

13. System comprising
a facility for producing and testing compositions for paints, varnishes, printing inks, grinding resins, pigment concentrates or other coating materials, where the facility comprises at least two workstations, where the at least two workstations are connected to one another via a transport system on which self-propelled transport vehicles are able to run for transporting the components of the composition and/or of the composition produced between the workstations, and a computer system configured to perform the method of claim 6.

14. A computer-implemented method for providing a coating composition related prediction program, the method comprising:
providing a database comprising associations of qualitative and/or quantitative characterizations of coating compositions in association with one or more parameters selected from the group comprising one or more of the components of the coating composition, relative and/or absolute amounts of one or more of the said components and/or manufacturing-process parameters of the coating composition;

training a machine learning program on the associations of the coating composition characterizations with the one or more parameters in the database for providing a predictive model (M2, M3) having learned to correlate qualitative and/or quantitative characterizations of one or more coating composition with one or more of the parameters stored in association with the respective coating components and/or manufacturing-process parameters used for generating the coating composition; and providing a composition-quality-prediction program which comprises the predictive model (M2), the composition-quality-prediction program being configured for using the predictive model (M2) for predicting the properties of a coating composition from one or more input parameters selected from the group comprising one or more components of a coating composition, relative and/or absolute amounts of one or more of the said components and/or manufacturing-process parameters, the properties including the detection of a phase separation; and/or providing a composition-specification-prediction program which comprises the predictive model (M3), the composition-specification-prediction program being configured for using the predictive model (M3) for predicting, based on an input specifying at least desired storage stability characterization and optionally one or more additional parameters related to the desired coating composition, in particular components, process parameters and application parameter, and outputting one or more parameters related to a coating composition predicted to generate a coating composition having the input storage characterizations and optionally meeting the additional parameters as input, the one or more parameters being selected from the group comprising one or more components of the said coating composition, relative and/or absolute amounts of one or more of the said components and/or manufacturing-process parameters to be used for preparing the coating composition.

15. The method of claim 14, the method comprising:
providing a plurality of force-displacement profiles related to coating compositions made from multiple different coating components, wherein at least some of the coating compositions respectively having one or more phases of multiple different types;

applying a phase-separation-identification program on the force-displacement profiles for recognizing force-displacement patterns in the force-displacement profiles, for obtaining the measures of the phases represented by the identified force-displacement patterns in the force-displacement profiles and for computing a qualitative and/or quantitative characterization of the coating compositions represented by the force-displacement profiles;

storing the qualitative and/or quantitative characterizations of the phases in association with one or more parameters related to the coating and/or process parameters used for creating the coating composition comprising these phases in the database.

* * * * *